United States Patent
Yoshimoto et al.

(10) Patent No.: US 10,160,973 B2
(45) Date of Patent: Dec. 25, 2018

(54) NUCLEIC ACID APTAMERS BINDING TO VASCULAR ENDOTHELIAL GROWTH FACTOR RECEPTORS

(71) Applicants: NISSAN CHEMICAL INDUSTRIES, LTD., Tokyo (JP); THE UNIVERSITY OF TOKYO, Tokyo (JP)

(72) Inventors: Keitaro Yoshimoto, Tokyo (JP); Keiko Kimura, Tokyo (JP); Hitoshi Furusho, Funabashi (JP)

(73) Assignees: NISSAN CHEMICAL INDUSTRIES, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/563,313

(22) PCT Filed: Mar. 28, 2016

(86) PCT No.: PCT/JP2016/059892
§ 371 (c)(1),
(2) Date: Sep. 29, 2017

(87) PCT Pub. No.: WO2016/158851
PCT Pub. Date: Oct. 6, 2016

(65) Prior Publication Data
US 2018/0066263 A1 Mar. 8, 2018

(30) Foreign Application Priority Data
Mar. 30, 2015 (JP) ................. 2015-068388

(51) Int. Cl.
| | | |
|---|---|---|
| C12N 15/11 | (2006.01) | |
| C12N 15/115 | (2010.01) | |
| A61K 48/00 | (2006.01) | |
| A61K 31/7088 | (2006.01) | |
| A61K 31/711 | (2006.01) | |
| A61K 31/712 | (2006.01) | |
| A61K 31/7125 | (2006.01) | |
| C12Q 1/02 | (2006.01) | |
| C12Q 1/68 | (2018.01) | |
| C12N 15/09 | (2006.01) | |
| G01N 33/50 | (2006.01) | |
| C12N 15/10 | (2006.01) | |
| G01N 33/53 | (2006.01) | |
| G01N 33/58 | (2006.01) | |
| G01N 33/74 | (2006.01) | |

(52) U.S. Cl.
CPC ........ *C12N 15/115* (2013.01); *A61K 31/7088* (2013.01); *A61K 31/711* (2013.01); *A61K 31/712* (2013.01); *A61K 31/7125* (2013.01); *A61K 48/00* (2013.01); *C12N 15/09* (2013.01); *C12N 15/1048* (2013.01); *C12Q 1/02* (2013.01); *C12Q 1/68* (2013.01); *G01N 33/50* (2013.01); *G01N 33/5308* (2013.01); *G01N 33/588* (2013.01); *G01N 33/74* (2013.01); *C12N 2310/16* (2013.01); *C12N 2310/3517* (2013.01); *G01N 2333/71* (2013.01); *G01N 2800/7014* (2013.01)

(58) Field of Classification Search
None
See application file for complete search history.

(56) References Cited

U.S. PATENT DOCUMENTS

| | | |
|---|---|---|
| 5,270,163 A | 12/1993 | Gold et al. |
| 5,639,736 A | 6/1997 | Robinson |
| 5,861,499 A | 1/1999 | Rockwell et al. |
| 6,762,290 B1 | 7/2004 | Janjic et al. |
| 2003/0175703 A1 | 9/2003 | Sullenger et al. |
| 2004/0224915 A1 | 11/2004 | Janjic et al. |
| 2005/0260153 A1 | 11/2005 | Calias et al. |
| 2005/0260651 A1 | 11/2005 | Calias et al. |

(Continued)

FOREIGN PATENT DOCUMENTS

| | | |
|---|---|---|
| EP | 2 743 349 A1 | 6/2014 |
| JP | 2007-532662 A | 11/2007 |

(Continued)

OTHER PUBLICATIONS

International Search Report for PCT/JP2016/059892 (PCT/ISA/210) dated May 10, 2016.
Jellinek et al., "Inhibition of Receptor Binding by High-Affinity RNA Ligands to Vascular Endothelial Growth Factor", Biochemistry, 1994, vol. 33, pp. 10450-10456.
Kim et al., "Aptamer-modified magnetic nanoprobe for molecular MR imaging of VEGFR2 on angiogenic vasculature", Nanoscale Research Letters, 2013, vol. 8, 10 pages.

(Continued)

*Primary Examiner* — Ekaterina Poliakova-Georgantas
(74) *Attorney, Agent, or Firm* — Birch, Stewart, Kolasch & Birch, LLP

(57) ABSTRACT

[Problem] To provide a novel nucleic acid aptamer for a vascular endothelial growth factor receptor, said nucleic acid aptamer being useful for the diagnosis and treatment of various diseases associated with VEGFs that can regulate angiogenesis and receptors for the VEGFs, e.g., tumor angiogenesis, diabetic retina and chronic rheumatoid arthritis.
[Solution] A nucleic acid aptamer characterized by comprising a nucleotide sequence represented by any one of SEQ ID NOs: 1 to 5, and also characterized by being capable of bonding to a human VEGF receptor specifically. In a preferred embodiment of the nucleic acid aptamer, a primer recognition sequence, a fluorescent label, or a biotin molecule, an avidin molecule, a streptavidin molecule or other specific binding tag peptide may be linked to the 5'- or 3'-terminal of the nucleic acid aptamer for the purpose of making it possible to detect the nucleic acid aptamer easily.

11 Claims, 1 Drawing Sheet
Specification includes a Sequence Listing.

(56) References Cited

U.S. PATENT DOCUMENTS

| | | |
|---|---|---|
| 2009/0208936 A1 | 8/2009 | Tan et al. |
| 2014/0194320 A1 | 7/2014 | Hirao et al. |

FOREIGN PATENT DOCUMENTS

| | | |
|---|---|---|
| WO | WO 91/19813 A1 | 12/1991 |
| WO | WO 95/04142 A2 | 2/1995 |
| WO | WO 95/21868 A1 | 8/1995 |
| WO | WO 01/09157 A1 | 2/2001 |
| WO | WO 02/26932 A2 | 4/2002 |
| WO | WO 2005/110489 A2 | 11/2005 |
| WO | WO 2006/074216 A2 | 7/2006 |

OTHER PUBLICATIONS

Matthews et al., "A receptor tyrosine kinase cDNA isolated from a population of enriched primitive hematopoietic cells and exhibiting close genetic linkage to c-kit", Proceedings of the National Academy of Sciences of the United States of America, 1991, vol. 88, pp. 9026-9030.

Ohuchi et al., "The RNA Aptamer Inhibiting Human Vesicular Endothelial Growth Factor Receptor 1 without Affecting Cytokine Binding", Biochemistry, 2013, vol. 52, pp. 2274-2279.

Sawano et al., "Flt-1 but not KDR/Flk-1 Tyrosine Kinase Is a Receptor for Placenta Growth Factor, Which Is Related to Vascular Endothelial Growth Factor", Cell Growth & Differentiation, Feb. 1996, vol. 7, pp. 213-221.

Shibuya et al., "Nucleotide sequence and expression of a novel human receptor-type tyrosine kinase gene (flt) closely related to the fms family", Oncogene, 1990, vol. 5, pp. 519-524.

White et al., "Generation of Species Cross-reactive Aptamers Using 'Toggle' SELEX", Molecular Therapy, Dec. 2001, vol. 4, No. 6, pp. 567-573.

Written Opinion of the International Searching Authority for PCT/JP2016/059892 (PCT/ISA/237) dated May 10, 2016.

Yang et al., "Advances in SELEX and application of aptamers in the central nervous system", Biomolecular Engineering, 2007, vol. 24, pp. 583-592.

Extended European Search Report dated Oct. 18, 2018, in European Patent Application No. 16772732.0.

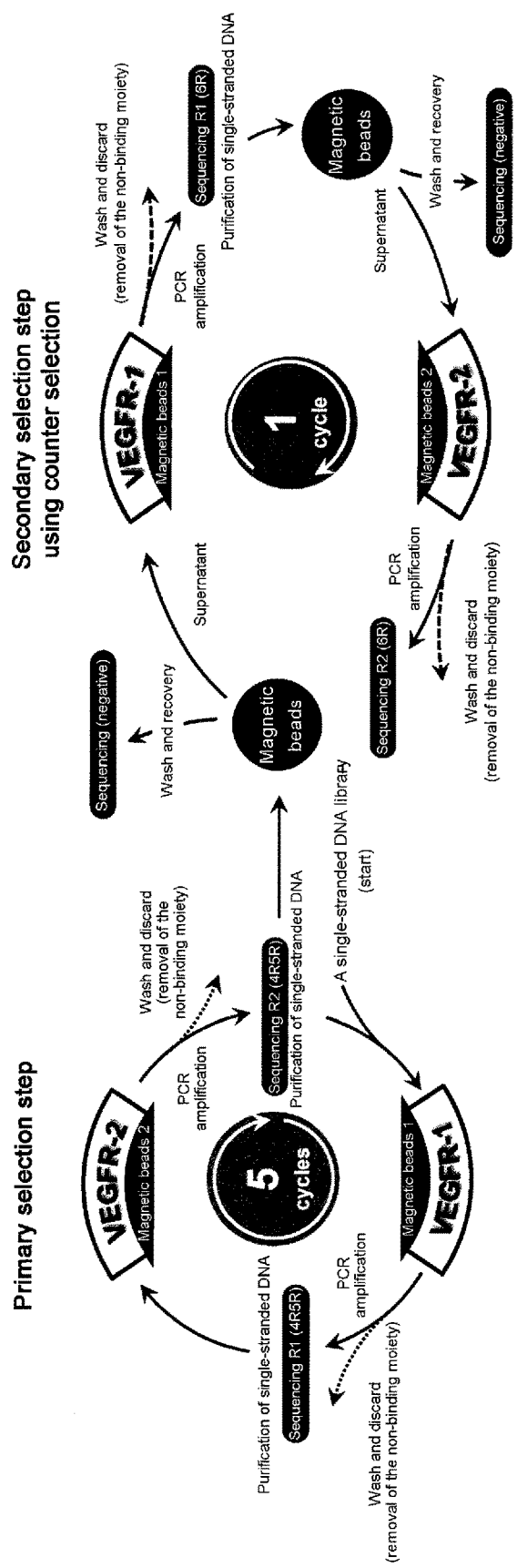

NUCLEIC ACID APTAMERS BINDING TO VASCULAR ENDOTHELIAL GROWTH FACTOR RECEPTORS

TECHNICAL FIELD

The present invention is related to nucleic acids that can specifically bind to vascular endothelial growth factor (VEGF) receptors and compositions comprising the same.

BACKGROUND ART

Angiogenesis is an important biological process not only under physiological conditions, but also in association with diseases such as tumor angiogenesis, diabetic retinopathy, and chronic rheumatoid arthritis. In angiogenesis, many signaling systems such as vascular endothelial growth factor (VEGF) and its receptor, angiopoietin-Tie receptor, ephrin-Eph4 receptor are involved. Among them, VEGF and its receptor, inter alia, plays an important role by being involved in the proliferation of vascular endothelial cells and the acceleration of vascular permeability.

VEGF is a proliferation factor specific for endothelial cells which is a 34 to 45 kDa dimeric glycoprotein formed by subunits with a molecular weight of approximately 20 kDa. VEGF has a wide range of activities such as promotion of vasculogenesis, enhancement of vascular permeability, and other activities. VEGF belongs to a platelet-derived growth factor (PDGF) family which is a growth factor and it has a homology of approximately 18% at an amino acid level with chain A and chain B of PDGF. Moreover, VEGF comprises the eight conservative cysteine residues common to all growth factors belonging to the PDGF family.

VEGF exerts an influence over vascular endothelial cells by binding to specific high-affinity cell surface receptors. In endothelial cells, 150 and 130 kDA receptors are identified. VEGF receptors belong to a super family of receptor tyrosine kinase (RTKs) which is characterized by a conserved cytoplasmic catalytic kinase domain and a hydrophilic kinase sequence. The extracellular domain of VEGF receptor is constituted from seven immunoglobulin-like domains that are believed to be involved in the VEGF binding function.

The two most abundant and high affinity receptors of VEGF are VEGFR1 (Flt-1) and VEGFR2 (KDR/Flk-1). VEGFR1 is a gene isolated for the first time by Shibuya et al., and this is called as fms-like tyrosine kinase (Flt-1) due to its structural similarity (Non-Patent Document 1). On the other hand, VEGFR2 has a lower affinity to VEGF as compared to VEGFR1; however, autophosphorylation occurs at a high level and the kinase activity of VEGFR2 is approximately of the same degree as other representative receptor kinases (Non-Patent Document 2). A mouse homolog of KDR has an 85% amino acid homology with KDR, which is called as flk-1 (fetal liver kinase-1) (Non-Patent Document 3). VEGFR2 which is expressed in endothelial cells and which is directly involved in pathological angiogenesis has little involvement in the development of inflammatory diseases. On the other hand, VEGFR1 which is expressed in monocytes and macrophage system is suggested to be deeply involved in inflammation via the mobilization and activation of the function of inflammatory cells.

Patent Document 1 discloses that VEGF expression is inhibited by using a certain kind of anti-sense oligonucleotide which targets a VEGF RNA. Non-Patent Document 4 discloses that the binding of VEGF to its receptor is inhibited by using a particular VEGF specific high affinity RNA aptamer. Patent Document 2 discloses that a certain kind of anti-VEGF receptor monoclonal antibody is used to neutralize the effect of VEGF on the endothelial cells. However, any base sequence of a nucleic acid aptamer that specifically binds to a VEGF receptor has not been reported.

For the screening of a novel aptamer specifically adsorbing to a protein or a cell, in vitro selection method is used as a most effective means. In particular, Systematic Evolution of Ligands by Exponential enrichment (SELEX) method is roughly divided into two steps: the selection of target nucleic acid molecules and the amplification of selected aptamers (for example, Patent Document 3). Nucleic acid fragments with high affinity can be obtained by repeating the selection and amplification with an increased selection pressure. Moreover, in the recent years, various modifications have been made, and superior methods and the like in efficacy and selectivity which allows the collection of aptamers with fewer number of cycles are reported. These aptamers have various advantages that cannot be found in antibodies such as the following: synthesis can be performed chemically and in a short period of time, the modification of molecules can be performed economically, the action mechanism is simple, and hardly any immunogenicity is reported, which are additional advantages other than the high-affinity and specificity to a target that are features of an antibody conventionally used in diagnosis and treatment.

PRIOR ART DOCUMENTS

Patent Documents

Patent Document 1: WO95/04142
Patent Document 2: WO95/21868
Patent Document 3: WO91/19813

Non-Patent Documents

Non-Patent Document 1: Shibuya et al., 1990, Oncogene 5, 519
Non-Patent Document 2: Sawano et al., 1996, Cell Growth Diff, 7, 213-221
Non-Patent Document 3: Mathews et al., 1991, Proc. Natl. Acad. Sci., USA, 88, 9026
Non-Patent Document 4: Jellinek et al., 1994, Biochemistry 33, 10450

SUMMARY OF INVENTION

Technical Problem

Based on such background, the present invention aims to reveal the details of the role of VEGF and the receptor of the same controlling angiogenesis, for example, precisely detecting the expression level of VEGF receptors in various cells and the function of VEGF receptors in live cells via monitoring over time and to provide novel nucleic acid aptamers against vascular endothelial growth factor receptors useful for diagnosis and treatment of diseases such as tumor angiogenesis, diabetic retinopathy, and rheumatoid arthritis that are various diseases associated to the above.

Solution to Problem

The present inventors have carried out dedicated research to solve the above-mentioned problem, thereby a nucleotide sequence having a specific binding ability to a VEGF receptor has been specified by using SELEX methods that utilizes magnetic particles. Accordingly, a nucleic acid having a specific sequence has been newly found to be able to function as a specific aptamer to a VEGF receptor, and thus, the present invention has been completed.

That is to say that, in one embodiment of the present invention, a nucleic acid aptamer comprising a nucleotide sequence shown in SEQ ID NOs: 1 to 5 and characterized by specifically binding to a VEGF receptor is provided. Here, when these aptamers are RNAs, in the base sequences of SEQ ID NOs: 1 to 5, T (thymine) is replaced by U (uracil). In a preferred embodiment of the present invention, the above-mentioned nucleic acid aptamer may be linked to a primer recognition sequence at it's 3' or 5' end, fluorescent labelling, biotin, avidin, or streptavidin, or to other specific binding tag peptides to facilitate the detection.

In another different embodiment of the present invention, a composition, a kit, or a method, for detecting human VEGF receptor, comprising the above-mentioned nucleic acid aptamer of the present invention is provided. A preferred embodiment is a method for diagnosing a disease associated to angiogenesis comprising a step of contacting the above-mentioned nucleic acid aptamer with a sample obtained from a living body selected from the group consisting of human endothelial cells, vascular tissues, blood, serum, and plasma and a step of detecting the presence of a human VEGF receptor by observing the response caused by the binding of the sample and the nucleic acid aptamer of the present invention.

In a further different embodiment of the present invention, the following is provided: a preventive or therapeutic pharmaceutical composition of a disease associated to angiogenesis comprising the above-mentioned nucleic acid aptamer of the present invention, the use of the above-mentioned nucleic acid aptamer of the present invention for preparation of such therapeutic pharmaceutical composition, or a therapeutic drug delivery system of a disease associated to angiogenesis comprising the nucleic acid aptamer of the present invention.

Advantageous Effects of the Invention

In accordance to the present invention, a nucleic acid aptamer can be provided as a useful and novel material which allows the detection of VEGF receptor and diagnosis of diseases associated to angiogenesis. That is to say that the provision of a novel nucleic acid aptamer that can specifically bind to a VEGF receptor can be used in the screening of the binding site of VEGF receptor and VEGF as well as in the analysis of angiogenesis and the mechanism of controlling angiogenesis.

BRIEF DESCRIPTION OF THE DRAWINGS

FIG. 1 is a schematic diagram showing the selection method of aptamers by SELEX method using VEGF receptors (VEGFR1 and VEGFR2) immobilized on the surface of magnetic microparticles.

DESCRIPTION OF EMBODIMENTS

Hereinafter, the embodiments of the present invention are described. Nonetheless, the scope of the present invention would not be restricted to these descriptions, and those other than the exemplifications mentioned below can be performed with appropriate modifications which are made without departing from the spirit of the present invention.

1. Nucleic Acid Aptamers

In the present specification, a "nucleic acid aptamer" is, for example, a nucleic acid molecule having a short sequence of approximately 20 to 200 base length and it refers to a single-stranded nucleic acid molecule that can specifically recognize a molecule and substance that would be a target. The nucleic acid aptamer according to the present invention is a single-stranded nucleic acid molecule having a function specifically binding to a VEGF receptor.

A binding target of the nucleic acid aptamer of the present invention includes a VEGF receptor, preferably, a human VEGF receptor, and more preferably, a human VEGF receptor 1 (VEGFR1), or a human VEGF receptor 2 (VEGFR2). VEGFR1 and VEGFR2 can be expressed in cultured cells and the like using a recombinant DNA technology, for example, and they are commercially available as reagents for investigations. In a typical embodiment, the nucleic acid aptamers according to the present invention include nucleotide sequences shown in SEQ ID NOs: 1 to 5 indicated below. Note that in the present specification, the nucleotide sequence is described from the left to the right, from 5' end to 3' end. Moreover, when the aptamer is an RNA, T is replaced by U in the above-mentioned nucleic acid sequence.

```
                                      <SEQ ID NO: 1>
5'-GTGATGGTCGGAGATGGATGGGGCAGCTTAGGTC-3'

<SEQ ID NO: 2>
5'-GTCGTGGCGGGGTTTTGTTTTGGTCGGGGGGTG-3'

<SEQ ID NO: 3>
5'-GGGGGGTGGGGTCGGGTGTTGGTCGTGGGGGCG-3'

<SEQ ID NO: 4>
5'-TAGGTGGGTTCGGGGGGTGCTGGTCGGGGGGTG-3'

<SEQ ID NO: 5>
5'-TGGGTTTAGGTTGGGTGGTTGGGTGGGGGGGCG-3'
```

The term "specific" in the present specification refers to a selective binding of a nucleic acid aptamer according to the present invention to a VEGF receptor. The binding specificity of an aptamer can be examined by comparing the binding of the aptamer to a VEGF receptor protein or cells expressing the VEGF receptor protein on the cell membrane to the binding of the aptamer to an irrelevant protein or cells, under a predetermined condition. The nucleic acid aptamer according to the present invention is considered as being specific, if the binding to the VEGF receptor is at least twice, at least five times, at least seven times, and preferably, at least ten times than the binding to an irrelevant protein or cells. An "irrelevant protein" is a protein that is different from a VEGF receptor protein, and the structure, function, and the like, of the protein could be different from the VEGF receptor. The binding manner of the specific binding is not particularly limited; however, it can include covalent bond, ionic bond, hydrogen bond, electrostatic or hydrophobic interaction, and the like.

The nucleic acid aptamer of the present invention may be the above-mentioned SEQ ID NOs: 1 to 5 in which one or more of nucleotides are substituted, deleted, or added, as long as the nucleic aptamer has the function to specifically bind to a human VEGF receptor. Preferably, the number of nucleotides that are substituted, deleted, or added are 1 to 3 nucleotide(s), more preferably 1 or 2 nucleotide(s), and further preferably 1 nucleotide.

Moreover, when such substitution, deletion, or addition of a nucleotide is present, the sequence of the nucleic acid aptamer of the present invention can have an identity of 90% or more, preferably 93% or more, or more preferably 96% or more, to each of the above-mentioned SEQ ID NOs: 1 to 5 (hereinafter, they can be referred to as "homologs"). Here, when used in the present specification, the term "sequence identity" is used with a meaning generally recognized in the present technical field. The term typically refers to the number of nucleotides of the nucleic acid sequence of the subject matter matching to the nucleotides identical to the reference nucleic acid sequence, when examined by a sequence analysis program (for example, Karlin and Altschul, 1990, PNAS 87:2264-2268; Karlin and Altschul, 1993, PNAS 90:5873-5877) or a visual inspection.

When one or more nucleotides are substituted, the substitution can be carried out by a universal base. The term "universal base" refers to a meaning that is generally recognized in the present technical field. The term, in general, refers to a nucleotide base analogue that forms a base pair with each base of a standard DNA/RNA with hardly any difference and which can be recognized by an intracellular enzyme (for example, Loakes et al., 1997, J. Mol. Bio. 270: 426-435). Non-limiting examples of universal bases include, C-phenyl, C-naphthyl, and other aromatic derivatives, inosine, azole carbozamide, and nitroazole derivatives (3'-nitropyrole, 4-nitroindole, 5-nitroindole, 6-nitroindole, and the like) (Loakes, 2001, Nucleic Acids Res. 29: 2437).

Furthermore, there is no upper limit on the length of the nucleic acid aptamer of the present invention as long as the nucleic acid aptamer has the function to specifically bind to a human VEGF receptor. However, in view of the easiness of synthesis and problems of antigenicity and the like, the length of the nucleic acid aptamer in the present embodiment, for example, as its upper limit, is 200 bases or less, preferably 150 bases or less, or more preferably 100 bases or less.

When the number of the total bases is low, chemical synthesis and bulk production are easier, and there is a greater advantage in terms of cost. In addition, it is easily chemically modified, the safeness in the living body is high, and toxicity is low. The lower limit is provided as a number that is the same or more to the number of the bases in the above-mentioned SEQ ID NOs: 1 to 5, i.e., 34 bases or more. A nucleic acid aptamer is preferably a single-stranded DNA (ssDNA); however, even in a case where a partial double-stranded structure is formed by taking a hairpin loop type structure, the length of that nucleic acid aptamer is calculated as a length of a single strand.

In a preferred embodiment, the nucleic acid aptamer of the present invention is any of the sequences selected from the group consisting of the nucleotide sequences of the above-mentioned SEQ ID NOs: 1 to 5, which can be a nucleotide sequence having a primer-primer recognition sequence at each 5' and 3' end. In other words, in this case, the nucleic acid aptamer has the following nucleotide sequence:

5'-$P_1$-X-$P_2$-3'.

Wherein X is a nucleotide sequence selected from the group consisting of the nucleotide sequences shown in SEQ ID NOs: 1 to 5 or is a sequence comprising 1 to 3 nucleotide substitutions, deletions, additions, in these sequences. $P_1$ and $P_2$ are a first and a second primer recognition sequence introduced for PCR amplification.

Preferably, $P_1$ is GCCTGTTGTGAGCCTCCT (SEQ ID NO: 6)
and
$P_2$ is CGCTTATTCTTGTCTCCC. (SEQ ID NO: 7)

The nucleic acid aptamer of the present invention may be chemically modified for an increase of the stability in the living body. Unlimited examples of such chemical modifications include a chemical substitution at the sugar chain moiety (for example, 2'-O methylation); a chemical substitution at the phosphate ester moiety (for example, phosphorothioation, amino group, lower alkyl amine group, and acetyl group), and a chemical substitution at a base moiety. Similarly, an additional base could be provided at the 5' or 3' end. The length of such additional base is normally 5 bases or less. Additional bases may be a DNA or RNA; however, when DNA is used, the stability of the aptamer may increase. Sequences of such additional bases include sequences such as ug-3', uu-3', tg-3', tt-3', ggg-3', guuu-3', gttt-3', ttttt-3', and uuuuu-3', for example; however, they are not limited thereto.

Furthermore, for example, the nucleic acid aptamer of the present invention can have a detection label linked to the 5' end or 3' end, for using it in the detection method of VEGF receptors or a kit used in the detection, as described hereinafter. As such detection label, fluorescent labelling is preferred; however, Raman label, enzyme label, and infrared label may be used.

In fluorescent labelling, fluorescent label agent conventionally used in the present technical field could be used; however, for example, fluorophores that can be introduced by commercially available oligonucleotide solid phase synthesis services include such as green fluorescent protein (GFP), fluorescent protein, fluorescein isothiocyanate (FITC), 6-carboxyfluorescein-aminohexyl, fluorescein derivative, Alexa Fluor 350, Alexa Fluor 405, Alexa Fluor 488, Alexa Fluor 647, Alexa Fluor 750, rhodamine, 6-carboxytetramethylrhodamine, (TAMRA (Registered Mark)), Phycoerythrin (PE), phycocyanin (PC), PC5, PC7, Cy dyes, Cy3, Cy3.5, Cy5, Cy5.5, Cy7, TexasRed, allophycocyanin (APC), aminomethyl coumarin acetate (AMCA), Marina Blue, Cascade Blue, Cascade Yellow, Pacific Blue, SPRD, Tetramethylrhodamine isothiocyanate (TRITC), R110, mC1B, CellTracker dyes, CFSE, JC-1, PKH, DCFH-DA, DHR, FDA, Calcein AM, nitrobenzoxadiazole (NBD) group, dimethylamino sulphonyl benzooxadiazole group, acridine(Acd), dansyl(Dns), 7-dimethylaminocoumarin-4-acetic acid (DMACA), 5-((2-Aminoethyl)amino)naphthalene-1-sulfonic acid (EDANS), naphthalene, anthracene, protoporphyrin 9, and the like.

Moreover, a quencher that absorbs a fluorescence energy emitted from the fluorescent substance may be further bound adjacent to a fluorescent substance. In such embodiment, fluorescence is detected by the fluorescent substance and quencher being separated at the time of detection reaction.

Examples of enzyme label include β-galactosidase, β-glucosidase, alkaliphosphatase, peroxidase, malate dehydrogenase, and the like. Moreover, as luminescent substrate, luminol, luminol derivative, luciferin, lucigenin, and the like may be used as a labelling agent.

For Raman scattering labelling, as a substituent having a binding ability with a metal surface which is located at the 5' end or 3' end, for example, of the above-mentioned fluorescent labelled aptamer, a thiol (SH) group, an alkylamino group, an aromatic amino group, and a carboxyl group can be introduced without being particularly limited thereto, and then, for example, these can be adsorbed onto the surface of a gold nanoparticle for the detection of an enhanced Raman scattering emitted from the gold particles with adsorbed aptamers, thereby cell recognition is carried out. In this case, without particular being limited thereto, gold, silver, copper, iron, silicon, quantum dots, and the like, can be used as metal nanoparticles.

2. Selection of Nucleic Acid Aptamers

The nucleic acid aptamer of the present invention can be selected and obtained by using a well-known in vitro selection method in the present technical field. As preferable examples of such method, Systematic Evolution of Ligands by Exponential enrichment: SELEX method is used.

SELEX method includes multiple repetition of selection of a nucleic acid ligand (aptamer) binding to a target substance and an exponential amplification by polymerase chain reaction (PCR), thereby a nucleic acid molecule (a single-stranded DNA, RNA) having an affinity to the target substance is obtained.

Moreover, apart from using them, the nucleic acid aptamer of the present invention can be selected and obtained using well-known methods in the present technical field.

As mentioned above, "in vitro selection method" is a method which selects aptamer molecules having an affinity to the target molecules and cells from a nucleic acid molecule pool containing random nucleotide sequences (e.g., DNA pool) and removes molecules which do not have an affinity. Furthermore, this is a method that allows the enrichment of an aptamer molecule having a strong binding ability by repeating the cycle which includes only amplifying the selected aptamer molecules using PCR methods and the like and performing the selection by affinity.

Specifically, first of all, a single-stranded nucleic acid fragment comprising a random nucleotide sequence (base sequence) region of approximately 20 to 300 bases, preferably, 30 to 150 bases, or more preferably 30 to 100 bases, is prepared. The preparation of a group of randomized single-stranded nucleic acid fragments can be carried out by a method of chemical nucleic acid synthesis, a synthetic method using an automated nucleic acid synthesizer, and synthetic method using amplification such as PCR, and the combination thereof. For the preparation of RNA from DNA, a single-stranded RNA library can be prepared by in vitro transcription with RNA polymerase such as T7RNA polymerase, for example, using a double-stranded DNA library as a template. In order to allow PCR amplification, these single-stranded nucleic acid fragments having base sequences that serve as primers at both ends are preferably used.

The primer recognition sequence moiety may have an appropriate restriction enzyme site so that the primer moiety could be excised by a restriction enzyme after a PCR amplification. The length of the primer recognition sequence moiety to be used is not particularly limited; however, it is approximately 20 to 50, preferably 20 to 30 bases. Moreover, for allowing the separation of a single-stranded DNA after PCR amplification by electrophoresis and the like, labelling such as with radioactive labelling and fluorescent labelling at the 5' end can be carried out.

Next, nucleic acid fragments having the random nucleotide sequence obtained as above (library pool) can be mixed with a target molecule immobilized onto a support such as magnetic microparticles at an appropriate concentration ratio, and this is incubated under an appropriate condition. After incubation, the mixture is centrifuged to separate the nucleic acid fragment-target molecule complex from free nucleic acid fragments. Then, the supernatant portion of the separated solution is removed and PCR reaction is carried out by using the single-stranded nucleic acid fragment collected from the obtained complex to perform the amplification of the target molecule binding nucleic acid sequence. Subsequently, a nucleic acid fragment which can form a complex with a target molecule can be made into a single strand according to the well-known methods in the present technical field. Such means include the separation utilizing the binding of streptavidin-immobilized magnetic particles with biotin, for example. Thereby, ssDNA having a cell binding ability can be separated from an amplified nucleic acid double-stranded chain, and moreover, unnecessary coexisting substance contained in the PCR reaction solution such as DNA polymerase could be removed. Thereafter, a similar operation is carried out using the collected ssDNA as a library pool.

A series of operations from mixing with the above-mentioned nucleic acid fragment and the target molecule, separating the nucleic acid fragment bound with the target molecule, PCR amplification, and using the amplified nucleic acid fragment once again in the binding with the target molecule is carried out for a couple of rounds. By repeating the rounds, a nucleic acid molecule which more specifically binds with a target cell can be selected. The sequence analysis of the obtained nucleic acid fragment can be carried out by the well-known methods in the present technical field.

Moreover, in the method for selecting (screening) the aptamer of the present invention, the above-mentioned target molecule preferably consists of a molecule of various kinds of proteins and the like constituting a family. Specifically, without being only limited to a VEGF receptor, a platelet-derived growth factor (PDGF) family, a placental growth factor (PlGF), and the like, are included; however, they are not limited thereto. In doing so, it is preferred that the above-mentioned round is repeated by alternatively using each molecule constituting the family. By performing such an operation, a nucleic acid aptamer binding to the conformational structural portion that is common to each protein family can be obtained, and by suppressing an unspecific binding, it is believed that the binding can take place at the structural portion responsible for the original function of each protein family.

Accordingly, in one embodiment of the present invention, a method for screening a nucleic acid aptamer comprising the following steps is provided, the method comprises:

(a) contacting a target molecule with various kinds of single-stranded nucleic acid fragments, to form a complex of the target molecule and the single-stranded nucleic acid fragment is formed;

(b) removing a single-stranded nucleic acid fragment not forming the complex;

(c) obtaining a group of candidate nucleic acid fragments comprising a single-stranded nucleic acid fragment obtained by the detachment of the complex;

(d) amplifying the group of candidate nucleic acid fragments;

(e) repeating the steps (a) to (d) several times;

(f) determining the base sequences of a group of candidate nucleic acid fragments after a predetermined number of repetition and specifying redundant nucleic acid fragments consisting of the base sequences detected redundantly;

(g) selecting the redundant nucleic acid fragments whose frequency of presence increases as the number of repetition in step (e) increases, wherein the target molecule is one of the various kinds of molecules constituting a family, and wherein the method is characterized by repeating step (e) by alternatively using each molecule.

Moreover, it is preferred that the method comprises a counter selection step in which the complex is formed by using a target molecule immobilized on a support, the group of candidate nucleic acid fragments obtained in step (e) is contacted with a support on which a target molecule is not immobilized, to further select a candidate nucleic acid fragment which does not form a complex with the support.

It is further preferred that the base sequences of the redundant nucleic acid fragments would not contain a base sequence of nucleic acid fragment that only binds to a support on which the target molecule is not immobilized.

3. Compositions for Detecting a VEGF Receptor, Methods for Detection, and Kit As mentioned above, the nucleic acid aptamer of the present invention has a function specifically binding to a VEGF receptor, and thus, it can be preferably used in the detection of the VEGF receptor. The composition for the detection comprising the nucleic acid aptamer of the present invention can also be used as a detection marker against cells expressing a VEGF receptor.

Specifically, the composition for detection comprising a nucleic acid aptamer of the present invention is contacted with samples obtained from the living body selected from the group consisting of endothelial cells, vascular tissues, blood, blood serum, and blood plasma. Then, the detection of the presence of a VEGF receptor is made by observing the response (presence of the signal) caused by the binding of the sample with the nucleic acid aptamer.

Samples obtained from the living body are obtained from animals; however, as long as the samples are samples or secreted body fluid that can be assured to be obtained at minimal invasion or in vitro cell culture solution component samples and the like, the form is not particularly restricted.

Moreover, the "response" for detecting the presence of a VEGF receptor is preferably a fluorescent response or a Raman scattering response, and as mentioned above, it is preferred to link the fluorescent labelling agent such as TAMRA (Registered Mark) and FITC at the 5' or 3' end of the nucleic acid aptamer in a fluorescence response. Furthermore, in the Raman scattering response, it is preferred that Cy3.5 (Registered Mark), TAMRA (Registered Mark), fluorescent labelling agent such as FITC are linked to the 5' end or 3' end of the nucleic acid aptamer, and the above-mentioned thiol (SH) group, alkylamino group, aromatic amino group, and carboxyl group are introduced, and for example, these can be adsorbed onto the surface of a gold nanoparticle.

The composition for detecting a VEGF receptor of the present invention can be provided as a kit comprising a nucleic acid aptamer enhancing the convenience or portability. In the kit, the nucleic acid aptamer can be provided in an embodiment of an aqueous solution in which the nucleic acid aptamer is generally dissolved at an appropriate concentration or in an embodiment of a DNA array in which the nucleic acid aptamer is immobilized on a solid phase support.

For example, biotin can be bound to the end of the nucleic acid aptamer to form a complex, streptavidin can be immobilized on the surface of a solid phase support, and the nucleic acid aptamer can be immobilized on the surface of the solid phase support by the interaction of biotin and streptavidin. The kit may appropriately contain other reagents and the like as necessary, and for example, additives such as solubilizing agents, pH adjusting agents, buffer agents, and tonicity agents can be used, and the formulation amount can appropriately be selected by those skilled in the art.

4. Pharmaceutical Composition and DDS

In another embodiment, the present invention provides a pharmaceutical composition for detecting a VEGF receptor, diagnosing or treating, comprising the above-mentioned nucleic acid aptamer. Preferably, in addition to the nucleic acid aptamer, the pharmaceutical composition can comprise an effective amount of a pharmaceutical compound for detecting a VEGF receptor, diagnosing or treating (an active ingredient) and a pharmaceutically acceptable carrier.

Other active ingredients contained in the pharmaceutical composition of the present invention is not particularly limited as long as it is effective for preventing or treating diseases associated to angiogenesis, for example, diabetic retinopathy, rheumatoid arthritis, or the like; however, it is preferably other angiogenesis inhibitors. Examples of such angiogenesis inhibitors include such as matrix metalloproteinase inhibitor, protein kinase C-β inhibitor, vascular endothelial growth factor (VEGF) inhibitor, basic FGF binding molecule, paclitaxel, rapamycin, fumagillin, doxorubicin, and other large number of agents.

Classes of agents that are commonly used to prevent atherosclerosis are collectively referred to as statins as they have the ability to control cholesterol levels. As these agents have an angiogenesis inhibitory ability as an additional property, they are useful as other pharmaceutical compounds in the pharmaceutical composition of the present invention.

Accordingly, the pharmaceutical composition of the present invention may include statins such as atorvastatin, simvastatin, lovastatin, pravastatin, and mevastatin. Typically, the pharmaceutical composition of the present invention is orally administered; however, it is also possible to employ parenteral administration. Other agents that are contained in the pharmaceutical composition of the present invention include antioxidants such as coenzyme Q, folic acids which reduce the homocysteine level, specific vitamin B's such as vitamin B6 and B12, nicotinic acid treatment, clofibrate, gemfibrozil, and fabric acid derivatives such as fenofibrate, cholesterol transport inhibitors such as probucol, non-absorbent resins such as cholestyramine and colestipol.

As a pharmaceutically acceptable carrier contained in the pharmaceutical composition of the present invention, for example, the following is included, but they are not restricted thereto: excipients such as sucrose and starch, binding agents such as cellulose and methylcellulose, disintegrating agents such as starch and carboxymethyl cellulose; lubricants such as magnesium stearate and aerosil; aromatic agents such as citric acid and menthol; preservatives such as sodium benzoate and sodium hydrogen sulfite; stabililzers such as citric acid and sodium citrate; suspending agents such as methyl cellulose and polyvinylpyrrolidone; dispersant such as surfactants; diluents such as water and saline, and base wax.

For promoting the delivery of the pharmaceutical composition of the present invention to target sites, the composition may further comprise a nucleic acid introducing reagent. As such nucleic acid introducing reagent, atelocollagen, liposomes, nanoparticles, cationic lipids such as lipofectin, lipofectamine, DOGS (transfectum), DOPE, DOTAP, DDAB, DHDEAB, HDEAB, polybrene, or polyethylene imine, can be used.

The pharmaceutical composition of the present invention, for example, can be administered to mammals (e.g., human, rat, mouse, rabbit, sheep, pig, cow, cat, dog, monkey, and the like).

The pharmaceutical composition of the present invention can be made into a large variety of formulation forms, for example, in a dosage form of capsules, tablets, and liquid agents. Although without being restricted, in general, it is made into a liquid to be made into an injection, or into an oral agent or a sustained release agent.

The injection could be prepared by well-known methods in the present technical field. For example, the injection could be prepared by dissolving the pharmaceutical composition of the present application in an appropriate solvent such as sterilized water, buffer solution, and saline, filtering this through a filter and the like for sterilization followed by filling into a sterile container.

Furthermore, as an oral agent, for example, the pharmaceutical composition of the present application could be formulated into a dosage form of tablets, granules, fine granules, powders, soft or hard capsules, liquid agents, emulsions, suspending agents, and syrups.

As a sustained release agent, for example, the pharmaceutical composition of the present application could be formulated into a dosage form of tablets, granules, fine granules, powders, soft or hard capsules, and microcapsules. At formulation, preferably, for example, stabilizers such as albumin, globulin, gelatin, mannitol, glucose, dextran, and ethylene glycol can be added.

Moreover, in the formulation of the pharmaceutical composition of the present invention, for example, necessary auxiliary additives such as excipients, solubilizing agents, anti-oxidants, soothing agents, and isotonic agents may be included.

Furthermore, when made into a liquid formulation, it is desirable that it is preserved by cryopreservation, freeze drying, or the like, where water is removed. The freeze dry agent is used with the addition of distilled water for injection and the like to be redissolved at the time when used.

Moreover, when made into a sustained release agent, as a carrier for sustained release, for example, soluble collagens or derivatives of soluble collagen, proteins such as gelatins, porous ceramics, polyamino acids, polylactic acids, chitin or chitin derivatives, water-absorbing polymer gel, can be used.

The pharmaceutical composition of the present invention may be administered by an appropriate administration route depending on its form. The administration can be carried out orally or parentally; however, when parentally administered, for example, the pharmaceutical composition can be administered in a form of injection by intravenous administration, arterial administration, subcutaneous administration, intramuscular injection, and the like. Furthermore, the pharmaceutical composition of the present application can be made into a form of a sustained release agent to be administrated by embedding into the living body, for example, to the affected site, under the skin, or in the muscle.

The amount of dose, the number of dose, and the like would be different depending on the purpose of administration, method of administration, kind and size of cancer, condition of the subject of administration (sex, age, weight, and the like); however, basically the administration is carried out according to the desirable administration form of the above-mentioned active ingredients.

Moreover, the nucleic acid aptamer of the present invention can be attached to or encapsulated in the surface of the transport material of liposomes, nanoparticles, and the like so that the pharmaceutical component contained in the transport material can be selectively transported to a VEGF receptor. Therefore, in a further embodiment, the present invention provides a drug delivery system for preventing or treating diseases associated to angiogenesis, in which the drug delivery system contains the above-mentioned nucleic acid aptamer.

EXAMPLES

Hereinafter, the present invention will be further described in detail with reference to the Examples, but the present invention is not limited thereto.

Example 1: Selection of the Aptamers

The selection of aptamers specifically binding to VEGFR1 and VEGFR2 from DNA pools having random sequences of 34 bases has been carried out using SELEX method. FIG. 1 show steps of SELEX method using magnetic particles. The details are as indicated below. Random DNA to be used is a single strand and this is hereinafter referred to as a sense strand. VEGFR1 and VEGFR2 which are the target molecules were purchased from R&D systems, which were immobilized on the magnetic particle surface manufactured by Pierce, and this was used.

For DNA pools (single-stranded DNA library in FIG. 1), an oligo DNA of a total length of 70 bases of the below-mentioned sequence in which 34 bases are the random sequence portion (N) was used.

DNA pool Random 34 (manufactured by Nihon Gene Research Laboratories)

SEQUENCE:
(SEQ ID NO: 8)
5'-GCCTGTTGTGAGCCTCCT(N34)CGCTTATTCTTGTCTCCC-3'

Length: 70 bases (random sequence corresponds to the 34 bases in the middle)
Molecular weight: 21391.3 g/mol
Molar absorption coefficient: 630475 L/mol·cm
The base sequences of both ends of the random sequence are primer sequences used in PCR.

The immobilization of VEGFR1 and VEGFR2 to the surface of the magnetic particles was carried out in accordance to the instruction manual attached to the magnetic particles.

Examples of SELEX Using Magnetic Particles

Seventeen µL of protein immobilized magnetic particles was measured, washed well with buffer I (phosphate buffer, pH 7.4, Ca, Mg free, 2 mM EDTA, 0.1% HSA) with the use of magnets. To this, 20 µL of a DNA pool prepared at a concentration of 10 µM was added and mixed at room temperature for 30 minutes. After this, target binding DNA and target non-binding DNA were separated by carrying out the washing for 3 times in buffer I using a magnet. Finally, the solution was substituted with 50 µL of TE buffer, heated at 95° C. for 10 minute, and the DNA adsorbed on protein immobilized magnetic particles was detached. As a sense strand DNA having protein binding ability is contained in the recovered supernatant, this was amplified by using PCR methods. The amplified DNA is of a double-stranded structure, and as a primer sequence forming an anti-sense strand is modified with biotin, only the target sense strand of this double strand was purified and recovered using a streptavidin immobilized magnetic particles. This recovered single-stranded DNA was once again mixed with a protein immobilized magnetic particles and the above-mentioned procedures were repeated. As shown in FIG. 1, first the above-mentioned procedures were performed on VEGFR1 immobilized magnetic particles, and subsequently, the above-mentioned operations were performed on VEGFR2 immobilized magnetic particles. This was considered as one cycle, and when a total of 4 and 5 cycles were carried out, the obtained DNA was analyzed using a Next Generation Sequencer (Ion Torrent PGM). The sequencing data obtained by this analysis are shown as R1-4R, R1-5R, R2-4R, and R2-5R.

Moreover, when the above-mentioned 5 cycles were performed, the obtained single-stranded DNA was mixed with magnetic particles that have not modified VEGFR1 or VEGFR2, and the supernatant was first recovered. Then, this was washed with buffer I for 3 times, the solution was finally substituted with 50 µL of TE buffer, and heated for 10 minutes at 95° C. As a result of this, DNA having a high affinity to unmodified magnetic particles was recovered. The DNA obtained therein was analyzed using a Next Generation Sequencer (Ion Torrent PGM). The sequence data obtained by this analysis was referred to as negative. Moreover, the supernatant recovered by the above-mentioned operations (a solution containing a single-stranded DNA with low affinity to magnetic particles) was mixed with VEGFR1 immobilized magnetic particles, and the operations of washing, heating/recovering, amplifying, and making into a single strand, which are the same as above, were performed. The DNA obtained therein was analyzed using a Next Generation Sequencer. The sequence data obtained by this analysis are shown as R1-6R. Then, the obtained single-stranded DNA was mixed with unmodified magnetic particles and the supernatant was first recovered. Then, this was washed with buffer I for 3 times, the solution was finally substituted with 50 µL of TE buffer, and heated for 10 minutes at 95° C. As a result of this, DNA having a high affinity to unmodified magnetic particles was recovered. Here, the obtained DNA was analyzed using a Next Generation Sequencer (Ion Torrent PGM). The sequence data obtained by this analysis was referred to as negative. Moreover, the supernatant recovered by the above-mentioned operations (a solution containing a single-stranded DNA with low affinity to magnetic particles) was mixed with VEGFR2 immobilized magnetic particles, and the operations of washing, heating/recovering, amplifying, and making into a single strand, which are the same as above, were performed. The DNA obtained here was analyzed using a Next Generation Sequencer. The sequence data obtained by this analysis are shown as R2-6R.

Examples of Sequence Data Analysis

The obtained sequence data, the number of sequence obtained in each of R1-4R, R1-5R, R2-4R, R2-5R, negative (×2), R1-6R, R2-6R, was analyzed using a software (CLC). Furthermore, these sequence data were exported, and a file combining these into one was prepared, and an aligned by using a software (ClustalX and the like). Based on the obtained analysis results, sequences which did not contain a negative sequence and which showed an increased presence ratio in the course of 4R to 6R were selected. The base sequences of the DNA aptamers selected by such are indicated below.

<No.11 (SEQ ID NO: 1)>
5'-GTGATGGTCGGAGATGGATGGGGCAGCTTAGGTC-3'

<No.17 (SEQ ID NO: 2)>
5'-GTCGTGGCGGGGTTTTGTTTTGGTCGGGGGGTG-3'

<No.18 (SEQ ID NO: 3)>
5'-GGGGGGTGGGGTCGGGTGTTGGTCGTGGGGGGCG-3'

<No.22 (SEQ ID NO: 4)>
5'-TAGGTGGGTTCGGGGGGTGCTGGTCGGGGGGTG-3'

<No.23 (SEQ ID NO: 5)>
5'-TGGGTTTAGGTTGGGTGGTTGGGTGGGGGGGCG-3'

<No.24 (SEQ ID NO: 9)>
5'-GGGGGAGTGATGTTGGGGTTGGGGGGTGGGGGCG-3'

Calculation of binding constant using a surface plasmon resonance sensor

The binding ability of the obtained nucleic acid aptamer to VEGFR1 and VEGFR2 was assessed using a surface plasmon resonance sensor (biacoreX). First, the operation written in the instruction manual was referred and the nucleic acid aptamers were immobilized on the surface of the sensor chip. Then, different concentrations of VEGFR1 or VEGFR2 proteins were injected and sensorgrams were obtained. These sensor grams were analyzed by single cycle analysis using software (BIA-evaluation) and dissociation constant such as shown in Table 1 was calculated.

TABLE 1

| Sequence Numbers | Base sequences (5' to 3') | VEGFR1 $K_d$ ($M^{-1}$) | VEGFR2 $K_d$ ($M^{-1}$) |
|---|---|---|---|
| No. 11 | GTGATGGTCGGAGATGGATGGGGCAGCTTAGGTC | $7.7 \times 10^{-12}$ SCA (25-5 nM) | $8.3 \times 10^{-8}$ SCA (300-19 nM) |
| No. 17 | GTCGTGGCGGGGTTTTGTTTTGGTCGGGGGGTG | $2.6 \times 10^{-10}$ SCA (50-10 nM) | $1.2 \times 10^{-8}$ SCA (100-12.5 nM) |
| No. 18 | GGGGGGTGGGGTCGGGTGTTGGTCGTGGGGGGCG | $1.2 \times 10^{-11}$ SCA (50-10 nM) | $1.7 \times 10^{-8}$ SCA (150-8 nM) |
| No. 22 | TAGGTGGGTTCGGGGGGTGCTGGTCGGGGGGTG | $7.6 \times 10^{-10}$ SCA (50-10 nM) | $3.1 \times 10^{-8}$ SCA (240-15 nM) |
| No. 23 | TGGGTTTAGGTTGGGTGGTTGGGTGGGGGGGCG | $3.8 \times 10^{-10}$ SCA (33-10 nM) | $1.5 \times 10^{-8}$ SCA (300-19 nM) |

SCA: single cycle analysis

Moreover, sequence data of the $1^{st}$ to $3^{rd}$ cycle was used and an analysis was carried out in the same manner as in 0072. The selected base sequences are indicated as below.

```
<No. 01 (SEQ ID NO: 10)>
5'-GTCGTGTTTGTTGTTGTTTTCATTTTTGCGGCCC-3'

<No. 02 (SEQ ID NO: 11)>
5'-GCTGATAGGATGGGTTGTAGGTCTAGGGGGGGCC-3'
```

The binding ability of the obtained nucleic acid aptamer to VEGFR1 and VEGFR2 was assessed using a surface plasmon resonance sensor (biacoreX). First, the operation written in the instruction manual was referred and the VEGFR1 was immobilized on the surface of the sensor chip when the binding between the VEGFR1 and nucleic acid aptamer was to be assessed. On the other hand, the nucleic acid aptamer was immobilized on the surface of the sensor chip when the binding between the VEGFR1 and nucleic acid aptamer was to be assessed. Then, different concentrations of nucleic acid aptamers or VEGFR2 proteins as shown in Table 2 were injected and sensorgrams were obtained. These sensor grams were analyzed by single cycle analysis using software (BIA-evaluation) and dissociation constants such as shown in Table 2 were calculated.

TABLE 2

| Sequence Numbers | Base sequences (5' to 3') | VEGFR1 $K_d$ ($M^{-1}$) | VEGFR2 $K_d$ ($M^{-1}$) |
| --- | --- | --- | --- |
| No. 11 | GTGATGGTCGGAGATGGATGGGGCAGCTTAGGTC | $5.12 \times 10^{-9}$ SCA (<20 nM) | $8.28 \times 10^{-8}$ SCA (<300 nM) |
| No. 17 | GTCGTGGCGGGGTTTTGTTTTGGTCGGGGGGTG | $1.19 \times 10^{-9}$ SCA (<20 nM) | $1.64 \times 10^{-7}$ SCA (<100 nM) |
| No. 18 | GGGGGGTGGGGTCGGGTGTTGGTCGTGGGGGGCG | $2.09 \times 10^{-9}$ SCA (<20 nM) | $1.69 \times 10^{-8}$ SCA (<150 nM) |
| No. 22 | TAGGTGGGTTCGGGGGGTGCTGGTCGGGGGGTG | $1.07 \times 10^{-9}$ SCA (<10 nM) | $3.10 \times 10^{-8}$ SCA (<240 nM) |
| No. 23 | TGGGTTTAGGTTGGGTGGTTGGGTGGGGGGGGCG | $9.22 \times 10^{-10}$ SCA (<10 nM) | $1.49 \times 10^{-8}$ SCA (<300 nM) |
| No. 24 | GGGGGAGTGATGTTGGGGTTGGGGGGTGGGGGCG | $3.53 \times 10^{-10}$ SCA (<20 nM) | $2.20 \times 10^{-8}$ SCA (<300 nM) |
| No. 1 | GTCGTGTTTGTTGTTGTTTTCATTTTTGCGGCCC | $3.32 \times 10^{-9}$ SCA (<20 nM) | $1.03 \times 10^{-7}$ SCA (<300 nM) |
| No. 2 | GCTGATAGGATGGGTTGTAGGTCTAGGGGGGGCC | $1.46 \times 10^{-9}$ SCA (<20 nM) | $3.15 \times 10^{-8}$ SCA (<300 nM) |

SCA: single cycle analysis

As obvious from these results, all of the above-mentioned DNA aptamers show a very interesting binding behavior in that they bind to both VEGFR1 and VEGFR2; however, it is understood that all of the DNA aptamers bind stronger to VEGFR1 than to VEGFR2. The reason to this is not clear; however, it is known that natural VEGF (VEGF-A) also binds stronger to VEGFR1 than to VEGFR2. In other words, as the DNA aptamer of the present invention shows a similar binding behavior as the natural ligand, its function as a VEGF inhibitor is suggested.

INDUSTRIAL APPLICABILITY

The nucleic acid aptamer of the present invention is easily chemically modified depending on the means for detection, such as fluorescent labeling, and thus, it has greater advantages than utilizing an antibody, in the preparation of a detection kit of VEGF receptor. Moreover, by conjugating drugs such as angiogenesis inhibitors, the drugs certainly can be allowed to act with a target site. Furthermore, as chemical synthesis can be easily carried out, a large scale culturing device such as for antibodies is not required, and for the advantage that it can reduce the trouble and cost for preparation, its industrial utility value is very high.

The invention claimed is:

1. A nucleic acid aptamer characterized by comprising any one of nucleic acid sequence selected from the group consisting of the nucleotide sequences shown in SEQ ID NOs: 1 to 5 and specifically binding to a vascular endothelial growth factor (VEGF) receptor, wherein the aptamer is a DNA or an RNA corresponding to the nucleotide sequences in SEQ ID NOs: 1 to 5, wherein the VEGF receptor is VEGFR1 and/or VEGFR2.

2. The nucleic acid aptamer according to claim 1, being a DNA aptamer.

3. The nucleic acid aptamer according to claim 1, comprising at least one chemical modification selected from the group consisting of a chemical substitution at a sugar chain moiety, a chemical substitution at a phosphate ester moiety, and a chemical substitution at a base moiety of nucleic acid.

4. The nucleic acid aptamer according to claim 1, having a fluorescent label at the 5' or 3' end.

5. The nucleic acid aptamer according to claim 1, wherein the nucleic acid aptamer is adsorbed on the surface of metal nanoparticles (quantum dot) being possible to emit fluorescence.

6. The nucleic acid aptamer according to claim 1, wherein the nucleic acid aptamer has a fluorescent label at 5' or 3' end, and wherein the labelled nucleic acid aptamer is adsorbed onto one or more kinds of particles selected from gold, silver, copper, iron, and silicon which are metals having a Raman scattering activity.

7. The nucleic acid aptamer according to claim 1, wherein the 5' end or 3' end is linked to biotin, avidin, or streptavidin, or to other specific binding tag peptides.

8. A composition for detecting human VEGF receptor, comprising the nucleic acid aptamer according to claim 1.

9. A kit for detecting human VEGF receptor, comprising the nucleic acid aptamer according to claim 1.

10. A method for diagnosing a disease associated to angiogenesis, comprising:
    contacting the nucleic acid aptamer according to claim 1 with a sample obtained from a living body selected from the group consisting of endothelial cells, vascular tissues, blood, blood serum, and blood plasma, and a step of detecting the presence of a VEGF receptor by observing the response caused by the binding of the sample and the nucleic acid aptamer.

11. The method for diagnosing according to claim 10, wherein the response is a fluorescent response.

* * * * *

SEQUENCE LISTING

<160> NUMBER OF SEQ ID NOS: 11

<210> SEQ ID NO 1
<211> LENGTH: 34
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 1
gtgatggtcg gagatggatg gggcagctta ggtc            34

<210> SEQ ID NO 2
<211> LENGTH: 33
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 2
gtcgtggcgg ggttttgttt tggtcggggg gtg             33

<210> SEQ ID NO 3
<211> LENGTH: 34
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 3 gggggggtggg gtcgggtgtt ggtcgtgggg ggcg           34

<210> SEQ ID NO 4
<211> LENGTH: 33
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 4
taggtgggtt cggggggtgc tggtcggggg gtg             33

<210> SEQ ID NO 5
<211> LENGTH: 34
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 5
tgggtttagg ttgggtggtt gggtgggggg ggcg            34

<210> SEQ ID NO 6
<211> LENGTH: 18
<212> TYPE: DNA
<213> ORGANISM: Artificial Sequence
<220> FEATURE:
<223> OTHER INFORMATION: First primer binding sequence

<400> SEQUENCE: 6
gcctgttgtg agcctcct                              18

<210> SEQ ID NO 7
<211> LENGTH: 18
<212> TYPE: DNA
<213> ORGANISM: Artificial sequence

```
<220> FEATURE:
<223> OTHER INFORMATION: Second primer binding sequence

<400> SEQUENCE: 7
cgcttattct tgtctccc                                              18

<210> SEQ ID NO 8
<211> LENGTH: 70
<212> TYPE: DNA
<213> ORGANISM: Artificial Sequence
<220> FEATURE:
<223> OTHER INFORMATION: DNA pool Random 34
<220> FEATURE:
<221> NAME/KEY: misc_feature
<222> LOCATION: (19)..(52)
<223> OTHER INFORMATION: n is a, g, c or t

<400> SEQUENCE: 8
gcctgttgtg agcctcctnn nnnnnnnnnn nnnnnnnnnn nnnnnnnnnn nncgcttatt    60
cttgtctccc                                                          70

<210> SEQ ID NO 9
<211> LENGTH: 34
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 9
gggggagtga tgttggggtt gggggtggg ggcg                              34

<210> SEQ ID NO 10
<211> LENGTH: 34
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 10
gtcgtgtttg ttgttgtttt catttttgcg gccc                             34

<210> SEQ ID NO 11
<211> LENGTH: 35
<212> TYPE: DNA
<213> ORGANISM: Artificial Sequence
<220> FEATURE:
<223> OTHER INFORMATION: DNA aptamer directed to VEGFR1 and VEGFR2

<400> SEQUENCE: 11
gctgatagga tgggttgtag gtctaggggg gggcc                            35
```